(12) United States Patent
Reinhardt

(10) Patent No.: US 7,833,285 B2
(45) Date of Patent: Nov. 16, 2010

(54) PROSTHETIC KNEE JOINT

(75) Inventor: Holger Reinhardt, Kempen (DE)

(73) Assignee: Bauerfeind AG, Zeulenroda (DE)

( * ) Notice: Subject to any disclaimer, the term of this patent is extended or adjusted under 35 U.S.C. 154(b) by 334 days.

(21) Appl. No.: 11/790,418

(22) Filed: Apr. 25, 2007

(65) Prior Publication Data
US 2007/0255426 A1 Nov. 1, 2007

(30) Foreign Application Priority Data
Apr. 28, 2006 (DE) ........................ 10 2006 019 858

(51) Int. Cl.
A61F 2/62 (2006.01)
(52) U.S. Cl. ......................................................... 623/39
(58) Field of Classification Search .................... 623/39
See application file for complete search history.

(56) References Cited
U.S. PATENT DOCUMENTS

| 4,320,747 | A | * | 3/1982 | Daniell, Jr. .................... 602/16 |
| 4,911,709 | A | * | 3/1990 | Marlow et al. ................. 623/39 |
| 5,376,138 | A | | 12/1994 | Bouchard et al. |
| 7,001,434 | B2 | * | 2/2006 | Van De Veen ................. 623/39 |
| 2005/0154473 | A1 | * | 7/2005 | Bassett ......................... 623/43 |
| 2005/0187506 | A1 | * | 8/2005 | Reinhardt ..................... 602/30 |

FOREIGN PATENT DOCUMENTS

| DE | 448 069 C | 8/1927 |
| DE | 89 10 199 U1 | 11/1989 |
| EP | 0 439 028 A2 | 7/1991 |
| EP | 0 672 398 A1 | 9/1995 |
| EP | 0 713 689 A1 | 5/1996 |

* cited by examiner

Primary Examiner—Bruce E Snow
Assistant Examiner—Melissa Montano
(74) Attorney, Agent, or Firm—Birch, Stewart, Kolasch & Birch, LLP

(57) ABSTRACT

The invention relates to a prosthetic knee joint with four pivot pins for connecting four joint members, said joint members each being supported at each of their ends in a pivot pin, wherein two opposite, transversely extending joint members are connectable at one end to a prosthetic stem and at the other end to a prosthetic foot, wherein the other two joint members as longitudinal joint members, in both the standing position and the bending position, are adapted to pivot essentially out of an angled position approximate to the parallel position into a relatively more greatly inclined position with respect to each other. At least one of the pivot pins of the joint member connected to the prosthetic foot is in the form of a rotatable, lockable eccentric, wherein, upon rotation of said eccentric, the distance between the two pivot pins on said joint member changes.

13 Claims, 6 Drawing Sheets $\Delta l$

PROSTHETIC KNEE JOINT

CROSS-REFERENCE TO RELATED APPLICATION

The present application claims priority under 35 U.S.C. §119 to German Patent Application No. 10 2006 019 858.1, filed Apr. 26, 2006, the entire contents of which are hereby incorporated by reference.

BACKGROUND OF THE INVENTION

1. Field of the Invention

The invention relates to a prosthetic knee joint with four pivot pins for connecting four joint members, said joint members each being supported at each of their ends in a pivot pin, wherein two opposite, transversely extending joint members are connectable at one end to a prosthetic stem and at the other end to a prosthetic foot, wherein the other two joint members as longitudinal joint members, in both the standing position and the bending position, are adapted to pivot essentially out of an angled position approximate to the parallel position into a relatively more greatly inclined position with respect to each other.

2. Description of Background Art

Such a prosthetic joint is published in DE 40 04 988 A1. In order to improve the standing stability of said prosthetic knee joint on the one hand and to facilitate bending of the knee on the other hand, one pivot pin, disposed in the joint member connected to the prosthetic foot, is supported in an oblong hole and is lockable therein by tightening a screw, whereby, in the case of an effectively increased distance between the pivot pins of said joint member, bending of the prosthesis is facilitated and, in the case of a shortening of the distance between the respective pivot pins through corresponding displacement in the oblong hole, the standing stability is increased. It has been demonstrated that, on the one hand, the permanent secure locking of the respective pivot pin, displaceable in the oblong hole, cannot always be guaranteed and that, on the other hand, the pivot pin in the oblong hole is unable, because of its basically exclusively linear contact with the inside surface of the oblong hole, to guarantee the required stability of the respective position of the pivot pin.

SUMMARY AND OBJECTS OF THE INVENTION

The object of the invention, therefore, is to support the movable pivot pin in the joint member connectable to the prosthetic foot such that said pivot pin always finds a large counter-bearing surface while, on the other hand, the variability of the position of the pivot pin is extended. The object of the invention is achieved in that at least one of the pivot pins of the joint member connected to the prosthetic foot is in the form of a rotatable, lockable eccentric, wherein, upon rotation of said eccentric, the distance between the two pivot pins on said joint member changes.

Where the pivot pin is in the form of an eccentric, this results in a larger support area for the pivot pin, said larger support area being capable of readily absorbing corresponding compressive forces. Furthermore, an eccentric offers the essential advantage that its change of position is possible by means of its rotation through 360°, i.e. it permits not only the shortening of the distance between the pivot pins, but directly also a relocation by 90° thereto, which is further of advantage in adapting the prosthetic knee joint to the wearer, because this may render it possible to a certain extent to make allowance for the height or change in height of the wearer owing to different heights of shoe. Such adaptation is of particular significance in the initial phase of use of a prosthetic knee joint, i.e. especially just after an operation, since, according to experience, this is the phase in which the wearer first of all looks for a high degree of standing stability, after achieving which they will then slowly proceed to walking with their prosthesis, for which purpose they can steplessly adjust the prosthetic knee joint, or have it adjusted, to their particular situation, which may also be dependent on psychological factors. The more active the patient is, the more dynamically the prosthetic knee joint can be adjusted.

It is additionally possible for more than one pivot pin to be in the form of an eccentric. This increases the flexibility of adaptation of the prosthetic knee joint to the existing situation of the wearer of the prosthesis and to certain changes arising from articles of clothing or shoes.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Illustrative examples of the invention are presented in the drawings, in which.

DETAILED DESCRIPTION OF THE PREFERRED EMBODIMENTS

Figure 1:
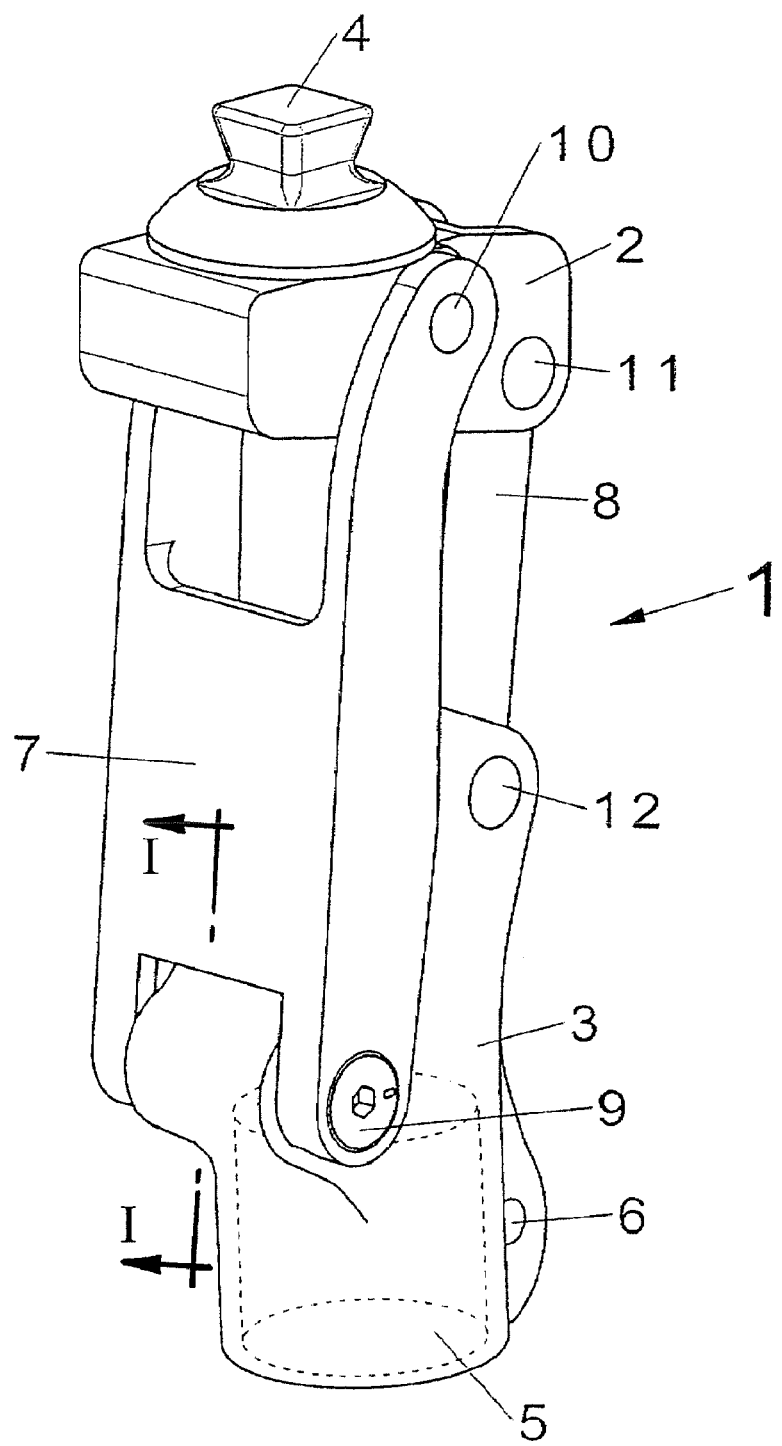
FIG. 1 shows a perspective view of the prosthetic knee joint.

The prosthetic knee joint 1 presented in FIG. 1 is provided, at one end, with the joint member 2 for connection to a prosthetic stem (not shown) and with the joint member 3 for connection to a prosthetic foot (not shown). Connection to the prosthetic stem is by means of the square pyramid adapter 4, onto which the prosthetic stem is screwed in known manner. For connection of the other joint member 3 to a prosthetic foot, the joint member 3 is provided with a hole 5 (drawn with dashed lines), which hole 5 is in known manner provided with a screw connector 6 and receives a stub which projects away from the prosthetic foot and which is lockable by means of the screw connector 6.

The two joint members 2 and 3 are connected to the two longitudinal joint members 7 and 8, each of which longitudinal joint members 7 and 8 are provided at their ends with pivot pins 9, 10, 11 and 12. The longitudinal joint members 7 and 8 are connected by means of said pivot pins to the transversely extending joint members 2 and 3. Consequently, this construction forms a prosthetic knee joint 1 of the kind basically employed in many prosthetic knee joints (see also the aforementioned DE 40 04 988 A1).

A special feature of the prosthetic knee joint presented in FIG. 1 is that the pivot pin 9 is in the form of an eccentric, the design and effect of which will be discussed in greater detail in connection with FIGS. 2 and 3.

Figures 2, 3:
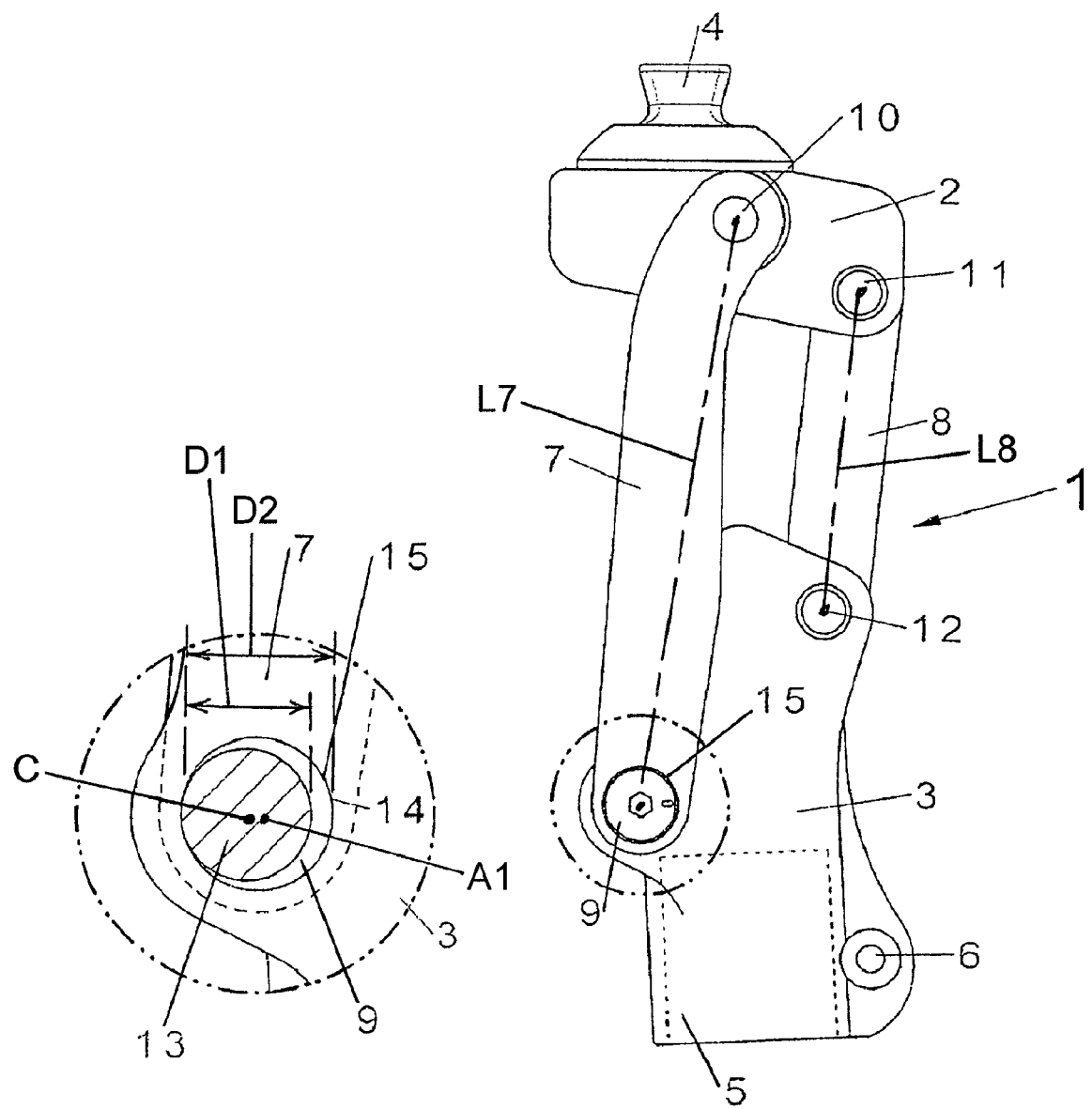
FIG. 2 shows the same prosthetic knee joint in a side elevation view.
FIG. 3 shows a vertical cross-section section as seen from the direction of lines I-I in FIG. 1, and cuts though the eccentric in a pivot pin.

Let reference be made first of all to FIG. 2, which presents the prosthetic knee joint 1 from FIG. 1 in a side elevation view. FIG. 2, which is a left side elevation view of the knee joint, shows one end of pivot pin 9 exposed in circular hole 15 formed in longitudinal joint member 7. The pivot pin 9 connects longitudinal joint member 7 to joint member 3 by extending from the left side of longitudinal joint member 7, through a hole in joint member 3, and ending in a hole similar to hole 15 on the right side of longitudinal joint member 7 (not shown). An eccentric 13 is formed in the portion of the pivot pin 9 extending through the hole in joint member 3, which is between the left and right ends of pivot pin 9. FIG. 3 shows a vertical cross-section of eccentric 13, joint member 3, and an inner face of the right end of pivot pin 9, which is held against the inner circumference 14 of hole 15 on the right side of longitudinal joint member 7. Eccentric 13 includes a circular outer circumference and an axial centerline C that is offset from and parallel to an axial centerline A1 of circular hole 15 in longitudinal joint member 7. The eccentric 13 has an outer diameter D1 that is smaller an inner diameter D2 of a circular hole 15 in the longitudinal joint member 7 within which pivot pin 9 is rotatable.

As initially explained, the effectiveness of the presented prosthetic knee joint 1 depends substantially on the distance between the pivot pins 9 and 12, because said distance both improves the standing stability and also facilitates the bending ability. To this end, the pivot pin 9 is in the form of an eccentric 13, which eccentric 13 is presented in section in FIG. 3. According to FIG. 3, the eccentric 13 is attached to the pivot pin 9 or grows out therefrom and forms with its outer surface the bearing surface with respect to the hole 15 in the longitudinal joint member 7. Depending on the rotation of the pivot pin 9 and therefore of the eccentric 13, said eccentric 13 moves around steplessly around the inner circumference 14 of the hole 15 and comes into contact each time with a different point of the hole 15, this providing the longitudinal joint member 7 with a correspondingly different position in relation to the joint member 3.

As pointed out above, in both the standing position and the bending position, the two longitudinal joint members 7 and 8 are adapted to pivot essentially out of an angled position approximate to the parallel position into a relatively more greatly inclined position with respect to each other. As shown in FIG. 3, for example, when the prosthetic knee joint 1 in the standing position is viewed in side view, a line L7 passing through centers on the pivot pins (10, 9) at the upper and lower end of longitudinal joint member 7 is substantially parallel to a line L8 passing through centers of the pivot pins (11, 12) at the upper and lower end of longitudinal joint member 8.

Figure 4:
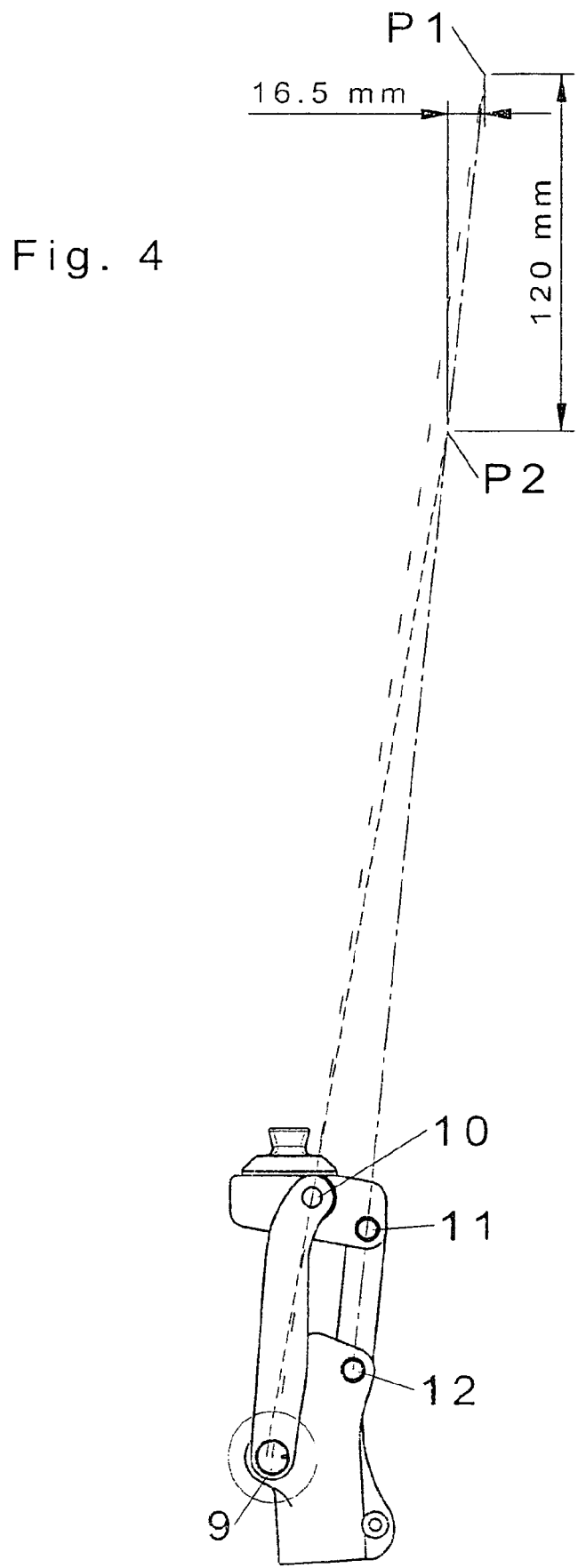
FIG. 4 shows the prosthetic knee joint with its instantaneous pivot point, which is dependent on the adjustment of the eccentric.
Figure 5A:
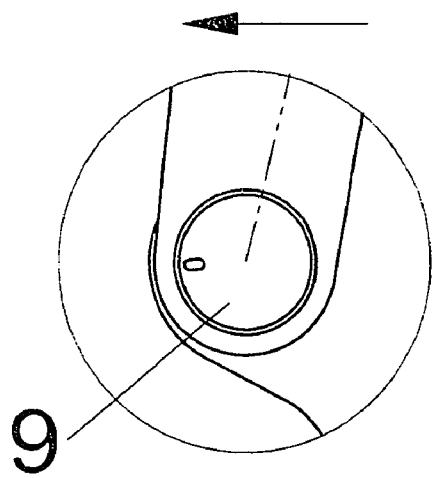
FIGS. 5a to 5d show four positions of the eccentric.
Figure 5B:
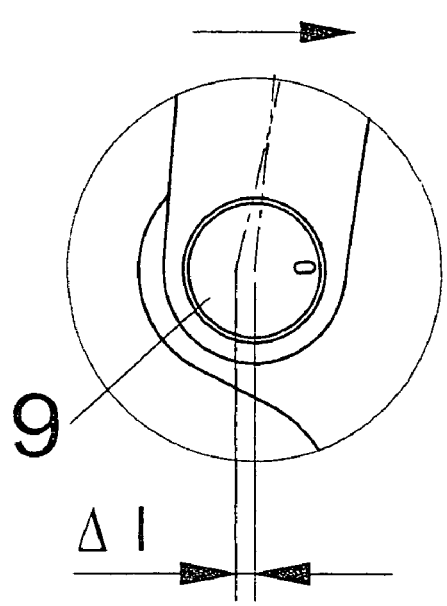
Figure 7:
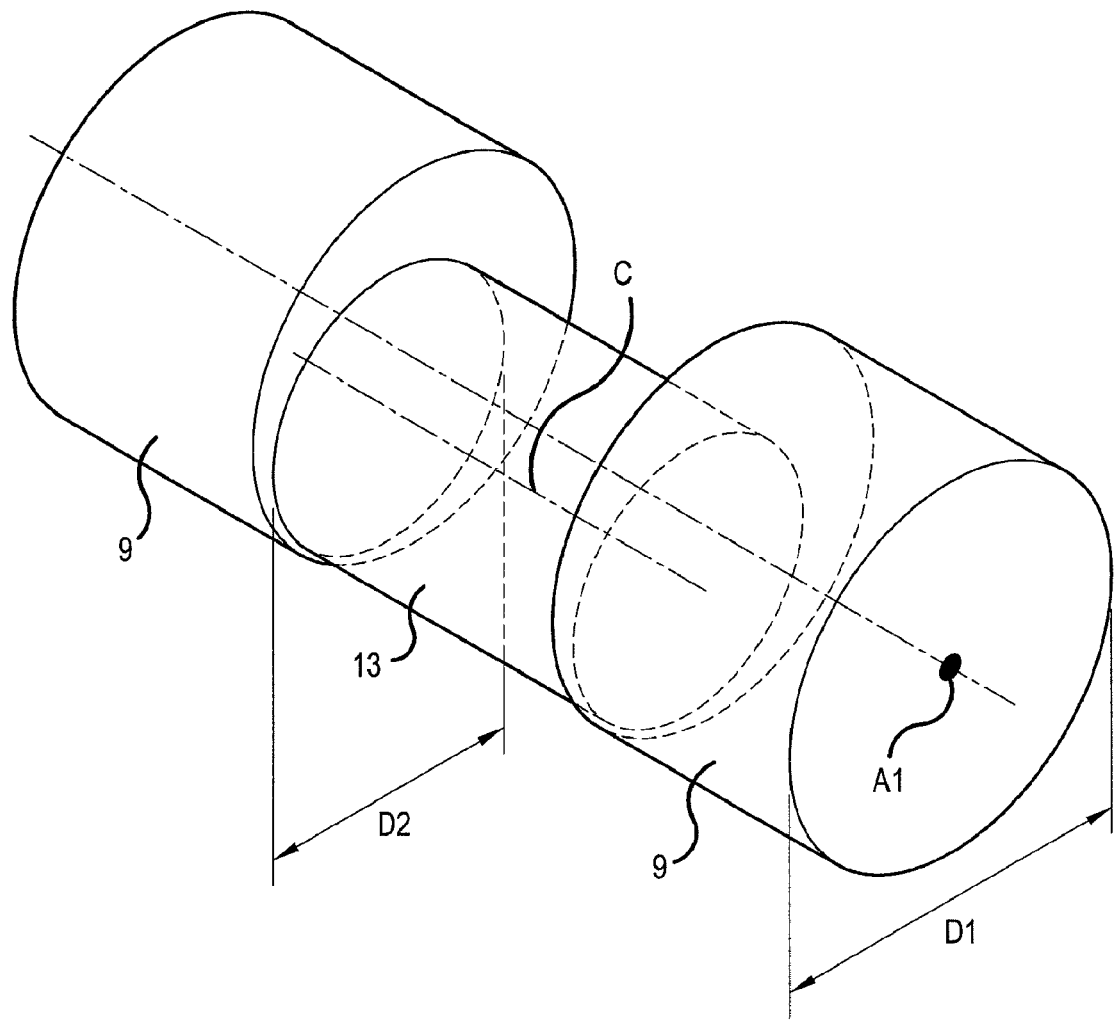
FIG. 7 shows an isometric view of the eccentric.

The consequences of such change of position of the eccentric 13 are presented in FIG. 4, which is based on the method of representation in DE 40 04 988 A1 (see FIG. 7 therein). FIG. 4 shows two extreme instantaneous pivot points P1 and P2, of which the instantaneous pivot point P1 is valid for a relatively short distance between the two pivot pins 9 and 12, whereas the instantaneous pivot point P2 is valid for the greatest distance between the two pivot pins 9 and 12. The corresponding positions of the eccentric 13 and of the pivot pin 9 (which carries said eccentric 13) are presented in detail in FIG. 5b (instantaneous pivot point P1) and in FIG. 5a (instantaneous pivot point P2).

Figure 5C:
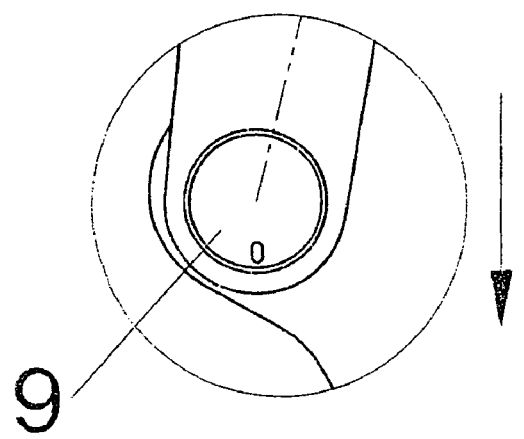
Figure 5D:
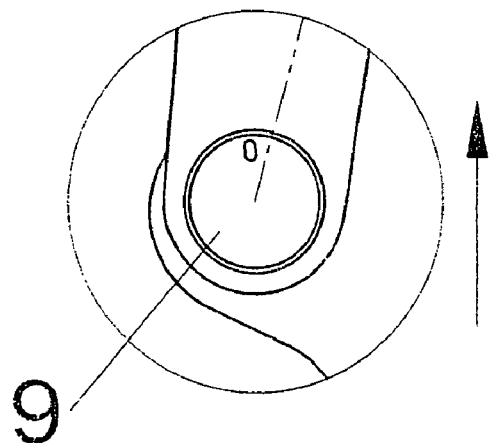

The positions of the pivot pin 9 and therefore of the eccentric 13 as presented in FIGS. 5c and 5d each represent a position of the pivot pin 9 in which said pivot pin 9 is at a different distance from the pivot pin 10 in order thereby additionally to permit a particular adjustment of Δ1 the attached prosthetic foot.

As is apparent, the steplessly adjustable position of the eccentric 13 results in each case in a particular adjustment Δ1 of the pivot pin 9 and therefore generally of the prosthetic knee joint 1, whereby said prosthetic knee joint 1 is adaptable to all possible necessary adjustments with regard to standing and moving as well as with regard to adaptation to any articles of clothing.

Figure 6:
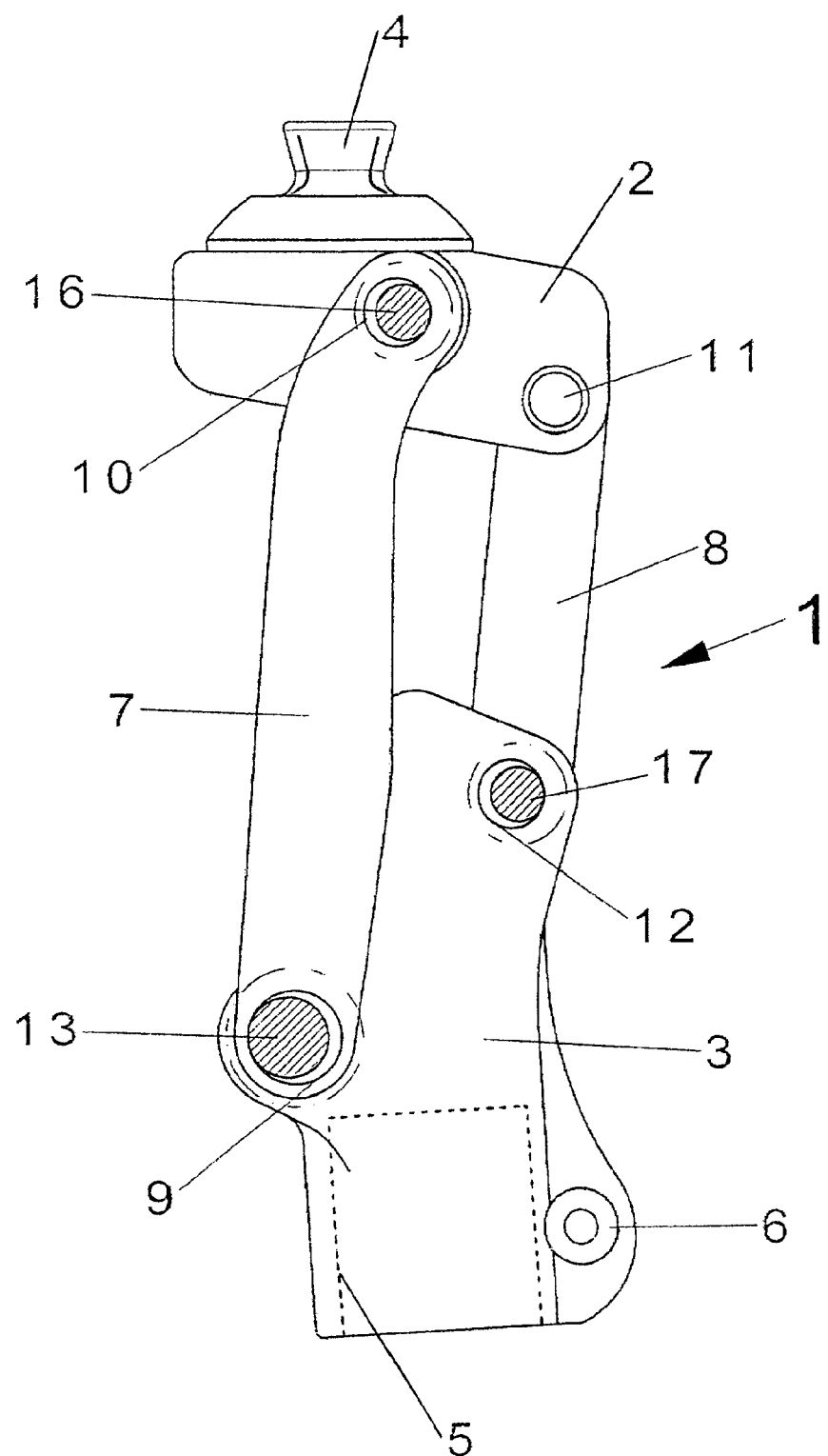
FIG. 6 shows a prosthetic knee joint with a eccentric provided on each of three pivot pins, and the eccentrics are shown in cross-sectional views.

FIG. 6 presents a variation on the configuration of the prosthetic knee joint from FIG. 2 in which, in addition to an eccentric in the pivot pin 9, the pivot pins 10 and 12 are also provided with eccentrics 16 and 17. This provides the prosthetic knee joint with further possibility of adaptation to different required positions.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. Prosthetic knee joint comprising:
   four joint members; and
   four pivot pins for connecting the four joint members,
   wherein two of the joint members are transversely extending joint members, one of which is connected at one end of the knee joint to a prosthetic stem, and the other of which is connected at an opposite end of the knee joint to a prosthetic foot,
   wherein the other two joint members are longitudinal joint members during movement of the knee joint,
   wherein the two longitudinal joint members are supported, respectively, at upper ends thereof by a pair of the pivot pins mounted to an upper one of the transversely extending joint members, and the two longitudinal joint members are supported, respectively, at lower ends thereof by another pair of the pivot pins mounted to a lower one of the transversely extending joint members,
   wherein the two longitudinal joint members being are adapted to pivot from a position substantially parallel to each other, into an inclined position with respect to each other,
   wherein at least a first one of the two pivot pins of the joint member which is connected to a prosthetic foot is formed as an eccentric,
   wherein the eccentric has an axial centerline C that is offset by a predetermined distance from a longitudinal axis A1 of an enlarged circular aperture, and is parallel to the longitudinal axis A1 of the enlarged circular aperture, and
   wherein, upon a first positioning of said eccentric relative to the enlarged aperture, a first predetermined distance between the first one and a second one of the two pivot pins on said joint member connected to the prosthetic foot is established, and
   wherein, upon a second positioning of said eccentric relative to the enlarged aperture, a second predetermined distance between the first one and a second one of the two pivot pins on said joint member connected to the prosthetic foot is established, the second predetermined distance being different from the first predetermined distance.

2. Prosthetic knee joint according to claim 1, wherein more than the first of one pivot pins is in a form of the eccentric.

3. Prosthetic knee joint according to claim 1, wherein only the first one of the pivot pins is in a form of the eccentric.

4. Prosthetic knee joint comprising:
four joint members; and
four pivot pins for connecting the four joint members,
wherein two of the joint members are transversely extending joint members, one of which is connected at one end of the knee joint to a prosthetic stem, and the other of which is connected at an opposite end of the knee joint to a prosthetic foot,
wherein the other two joint members are longitudinal joint members during movement of the knee joint,
wherein the two longitudinal joint members are supported, respectively, at upper ends thereof by a pair of the pivot pins mounted to an upper one of the transversely extending joint members, and the two longitudinal joint members are supported, respectively, at lower ends thereof by another pair of the pivot pins mounted to a lower one of the transversely extending joint members,
wherein the two longitudinal joint members are adapted to pivot from a position substantially parallel to each other, into an inclined position with respect to each other,
wherein at least a first one of the two pivot pins of the joint member is connected to the prosthetic foot is formed as an eccentric,
wherein the eccentric is formed with an outer diameter D1 that is smaller than an diameter D2 of a circular hole in each of the two longitudinal joint members, and
wherein the eccentric has an axial centerline C that is offset by a predetermined distance from a longitudinal axis A1 of an enlarged circular aperture, and is parallel to the longitudinal axis A1 of the enlarged circular aperture, and
wherein, upon a first positioning of said eccentric relative to the enlarged aperture, a first predetermined distance between the first one and a second one of the two pivot pins on said joint member connected to the prosthetic foot is established, and
wherein, upon a second positioning of said eccentric relative to the enlarged aperture, a second predetermined distance between the first one and a second one of the two pivot pins on said joint member connected to the prosthetic foot is established, the second predetermined distance being different from the first predetermined distance.

5. Prosthetic knee joint comprising:
four joint members; and
four pivot pins for connecting the four joint members,
wherein two of the joint members are transversely extending joint members, one of which is connected at one end of the knee joint to a prosthetic stem, and the other of which is connected at an opposite end of the knee joint to a prosthetic foot,
wherein the other two joint members are longitudinal joint members during movement of the knee joint,
wherein the two longitudinal joint members are supported, respectively, at upper ends thereof by a pair of the pivot pins mounted to an upper one of the transversely extending joint members, and the two longitudinal joint members are supported, respectively, at lower ends thereof by another pair of the pivot pins mounted to a lower one of the transversely extending joint members,
wherein the two longitudinal joint members are adapted to pivot from a position substantially parallel to each other, into an inclined position with respect to each other,
wherein at least a first one of the two pivot pins of the joint member is connected to the prosthetic foot is formed an eccentric,
wherein the eccentric has an axial centerline C that is offset by a predetermined distance from a longitudinal axis A1 of an enlarged circular aperture, and is parallel to the longitudinal axis A1 of the enlarged circular aperture, and
wherein, upon a first positioning of said eccentric relative to the enlarged aperture, a first predetermined distance between the first one and a second one of the two pivot pins on said joint member connected to the prosthetic foot is established, and
wherein, upon a second positioning of said eccentric relative to the enlarged aperture, a second predetermined distance between the first one and a second one of the two pivot pins on said joint member connected to the prosthetic foot is established, the second predetermined distance being different from the first predetermined distance,
wherein when the prosthetic knee joint is viewed in a side view, a line L7 passing through centers on the pivot pins at the upper and lower end of one of the longitudinal joint members is substantially parallel to a line L8 passing through centers of the pivot pins at the upper and lower end of the other of the longitudinal joint member,
wherein line L7 and line L8 intersected at one or the other of two points P1, P2, depending of positioning of the eccentric.

6. Prosthetic knee joint according to claim 1, further comprising a locking mechanism for locking the knee joint in a predetermined position.

7. Prosthetic knee joint according to claim 6, wherein the locking is disposed in a position below each of the pivot pins.

8. Prosthetic knee joint according to claim 4, further comprising a locking mechanism for locking the knee joint in a predetermined position.

9. Prosthetic knee joint according to claim 8, wherein the locking is disposed in a position below each of the pivot pins.

10. Prosthetic knee joint according to claim 4, wherein only the first one of the pivot pins is in a form of the eccentric.

11. Prosthetic knee joint according to claim 5, further comprising a locking mechanism for locking the knee joint in a predetermined position.

12. Prosthetic knee joint according to claim 11, wherein the locking is disposed in a position below each of the pivot pins.

13. Prosthetic knee joint according to claim 5, wherein only the first one of the pivot pins is in a form of the eccentric.

* * * * *